United States Patent
Keyak

(10) Patent No.: US 9,245,069 B2
(45) Date of Patent: Jan. 26, 2016

(54) METHODS FOR CALCULATING BONE FRACTURE LOAD

(71) Applicant: The Regents of the University of California, Oakland, CA (US)

(72) Inventor: Joyce H. Keyak, Orange, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 432 days.

(21) Appl. No.: 13/758,894

(22) Filed: Feb. 4, 2013

(65) Prior Publication Data

US 2013/0204595 A1    Aug. 8, 2013

Related U.S. Application Data

(60) Provisional application No. 61/594,945, filed on Feb. 3, 2012.

(51) Int. Cl.
*G06G 7/48* (2006.01)
*G06F 17/50* (2006.01)
*G06F 19/00* (2011.01)

(52) U.S. Cl.
CPC ........ *G06F 17/5018* (2013.01); *G06F 19/3437* (2013.01)

(58) Field of Classification Search
CPC .......... G06K 9/00; G06K 9/62; A61B 10/00; A61B 5/05; A61B 19/00; A61B 5/103; A61K 33/42; G01N 3/00; A61C 8/00; A61F 2/28
See application file for complete search history.

(56) References Cited

U.S. PATENT DOCUMENTS

| | | | |
|---|---|---|---|
| 6,442,287 B1 * | 8/2002 | Jiang et al. | 382/128 |
| 2005/0010106 A1 * | 1/2005 | Lang et al. | 600/425 |
| 2006/0075826 A1 * | 4/2006 | Roberts et al. | 73/788 |
| 2007/0082062 A1 * | 4/2007 | LeGeros | 424/602 |
| 2007/0238969 A1 * | 10/2007 | Song et al. | 600/410 |
| 2008/0294269 A1 * | 11/2008 | Fell | 623/23.48 |
| 2011/0117522 A1 * | 5/2011 | Verma et al. | 433/174 |
| 2012/0141596 A1 * | 6/2012 | Lally | 424/602 |

OTHER PUBLICATIONS

Bayraktar et al, "Comparison of the elastic and yield properties of human femoral trabecular and cortical bone tissue," J Biomech 2004; 37:27-35.

Bessho et al., "Prediction of proximal femur strength using a CT-based nonlinear finite element method: Differences in predicted fracture load and site with changing load and boundary conditions," Bone 2009; 45:226-231.

(Continued)

*Primary Examiner* — Kandasamy Thangavelu
(74) *Attorney, Agent, or Firm* — McDermott Will & Emery LLP

(57) ABSTRACT

Methods are provided for modeling structural behavior of a bone. For example, the methods can model the structural behavior of a femur, and in particular, a proximal femur, under conditions representing a fall onto the greater trochanter of the proximal femur. In such an embodiment, the method can comprise determining a strength of the femur, by a processor and based on (a) the elastic modulus, (b) the cortical bone yield strength, (c) the stress level $\sigma_{min}$, and (d) the post-yield stress-strain slope of the proximal femur.

22 Claims, 3 Drawing Sheets

(56) References Cited

OTHER PUBLICATIONS

Bessho et al., "Prediction of strength and strain of the proximal femur by a CT-based finite element method," J Biomech 2007; 40:1745-53.

Bevill et al., "Side-artifact errors in yield strength and elastic modulus for human trabecular bone and their dependence on bone volume fraction and anatomic site," J Biomech 2007; 40:3381-3388.

Ito et al., "Spinal trabecular bone loss and fracture in American and Japanese women," Calcif Tissue Int 1997; 61: 123-8.

Keaveny et al., "Biomechanics of trabecular bone," Annu Rev Biomed Eng 2001; 3:307-333.

Keller, "Predicting the compressive mechanical behavior of bone," J Biomech 1994; 27:1159-68.

Keyak "Improved prediction of proximal femoral fracture load using nonlinear finite element models," *Med Eng Phys 2001*; 23:165-173.

Keyak "Letter to the Editors," *J Orthop Res* 2000; 18(2):337.

Keyak et al., "Predicting proximal femoral strength using structural engineering models," *Clin Orthop Relat Res* 2005; 437:219-228, 2005.

Keyak et al., "Predicting the strength of femoral shafts with and without metastatic lesions," Clin Orthop Relat Res 2005; 439:161-70.

Keyak et al., "Prediction of femoral fracture load using automated finite element modeling," *J Biomech* 1998; 31:125-133.

Keyak et al., "Reduction in proximal femoral strength due to long-duration spaceflight," Bone 2009; 44:449-53.

Oden et al., "Effect of local density changes on the failure load of the proximal femur," J Orthop Res 1999; 17(5):661-7.

Orwoll et al "Finite element analysis of the proximal femur and hip fracture risk in older men," J.Bone Miner.Res. 2009; 24: 475-483.

Reilly et al., "The elastic and ultimate properties of compact bone tissue" J Biomech 1975; 8:393-405.

Un et al., "The effects of side-artifacts on the elastic modulus of trabecular bone," J Biomech 2006; 39:1955-1963.

\* cited by examiner

METHODS FOR CALCULATING BONE FRACTURE LOAD

CROSS-REFERENCE TO RELATED APPLICATIONS

This application claims the benefit of U.S. Provisional Application No. 61/594,945, filed Feb. 3, 2012, the entirety of which is incorporated herein by reference.

BACKGROUND

Some techniques have been developed to analyze and predict behavior of a bone as described by a force versus displacement curve. The present disclosure relates to improvements in methods of a structural engineering technique called finite element ("FE") analysis for modeling bone structural behavior to predict bone strength or "fracture load."

SUMMARY

Described herein are methods and systems for estimating the strength of a bone for assessing osteoporosis, the risk of bone fracture, or other applications for which the fracture load of the bone is important.

For example, improvements in methods of modeling bone structural behavior to predict bone fracture load can be applied to various types of loading conditions, such as single-limb stance loading and loading representing a fall, including a fall onto the greater trochanter, to predict the proximal femur fracture load.

The methods and systems can be used to estimate the strength of the hip (i.e., the proximal femur) for assessing osteoporosis, the risk of hip fracture, or other applications for which the strength or fracture load of the hip is important. Further, some embodiments of the methods disclosed herein can be used to calculate the strength or fracture load of any of a variety of bones, including long bones, such as the femur, tibia, humerus and radius, to name a few. Other bones can also be analyzed, including flat bones and vertebrae. Furthermore, the methods and systems disclosed herein can be used for bones of non-human species, e.g., animals used in research and development of drugs, etc.

Various embodiments provide computer implemented methods for modeling structural behavior of a bone under a specified loading condition. Such embodiments allow a clinician to determine a strength or fracture load of the bone, by a processor.

Bone fracture load can also be calculated based on (a) an elastic modulus, (b) a cortical bone strength, (c) a stress level $\sigma_{min}$ at perfectly plastic behavior, and (d) a post-yield stress-strain slope. The fracture load can comprise a peak strength.

Further, in some embodiments, bone fracture load can also be determined by (a) calculating an apparent ash density of bone based on imaging data, (b) determining cortical bone yield strength as a fraction of trabecular bone yield strength, based on the ash density, and then (c) determining a fracture load of the bone, by a processor, based on the cortical bone yield strength.

Further, some methods can be provided for evaluating the efficacy of a drug in increasing bone strength or fracture load to reduce fracture risk in a patient. For example, a first bone fracture load can be calculated. Then, after a drug therapy, a second bone fracture load can be calculated. The first bone fracture load and the second bone fracture load can then be compared to determine an effect of the drug therapy on bone fracture load. The first and second bone fracture loads can each be determined in accordance with the teachings herein.

In addition, some embodiments provide methods of modeling the structural behavior of a bone, under a loading condition, such as a displacement (which can be modeled as a series of smaller displacements), beyond bone fracture. The method can comprise determining, by a processor, a pre-fracture displacement of a bone and corresponding pre-fracture load supported by the bone for a given pre-fracture displacement. A maximum load supported by the bone prior to bone fracture can then be determined. Thereafter, a post-fracture displacement and corresponding post-fracture load supported by the bone for a given post-fracture displacement can also be determined.

In some embodiments, the post-fracture load can decrease with increasing post-fracture displacement. Further, the determination of the corresponding pre-fracture load supported by the bone can be based on (a) the elastic modulus, (b) the cortical bone strength, (c) the stress level $\sigma_{min}$, and (d) the post-yield stress-strain slope, for one or multiple parts of the bone.

For example, some methods can enable the clinician to model the structural behavior of a femur under a displacement or loading condition representing a fall onto the greater trochanter of the femur, by a processor, beyond bone fracture. The method can comprise the steps of: determining, by a processor, a pre-fracture displacement of a femur and corresponding pre-fracture load supported by the femur for a given pre-fracture displacement; determining a maximum load supported by the femur prior to femur fracture; and determining a post-fracture displacement and corresponding post-fracture load supported by the femur for a given post-fracture displacement; wherein the post-fracture load decreases with increasing post-fracture displacement.

In some embodiments, the post-yield stress-strain slope of bone or bone material can be determined based on the density. In some embodiments, the post-yield stress-strain slope of the bone can be determined based on a plurality of densities. The post-yield stress-strain slope can be less than zero. The stress-strain curve can have a negative slope after a peak.

Using the stress-strain curve, a region of perfectly plastic behavior at a stress level $\sigma_{min}$ is specified beyond a region of the post-yield stress-strain slope of the bone.

The stress level $\sigma_{min}$ can be determined as the product of X and S, where S is the strength of the bone. X can be between from about 0.22 to about 0.62. In some embodiments, X can be between from about 0.32 to about 0.52. Further, X can be between from about 0.37 to about 0.47. For example, X can be about 0.42.

The elastic modulus (E) can be determined using an imaging technique based on a bone density at each of a plurality of regions of the bone. In some embodiments, the bone strength or fracture load can be determined while maintaining an elastic modulus of the bone constant for all loading conditions.

The cortical bone strength or yield strength of a cortical bone can be determined as a fraction of a trabecular bone yield strength. The fraction can range from about ⅓ to about ⅔, such as from about 40% to about 60%. The fraction can be about ½ or about 50%.

The trabecular bone yield strength can be calculated as $102*(\text{ash density})^{1.5}$. Ash densities of the bone or bone material can be calculated using imaging data. For example, the ash density can be calculated as $0.00088703*(\text{den})+0.063343$, where den is the calcium hydroxyapatite (CHA)

quantitative-computed-tomography-measured equivalent density. The ash density of trabecular bone can be less than or equal to about 0.6037 g/cm$^3$.

Some embodiments provide a computer implemented method for modeling structural behavior of a proximal femur under loading representing forces due to a fall onto the greater trochanter of the proximal femur. The method can comprise: determining an elastic modulus (E) based on a bone density of the proximal femur determined by an imaging technique; determining a yield strength of cortical bone of the proximal femur as a fraction of a trabecular bone yield strength; determining, based on the density, a post-yield stress-strain slope of the proximal femur; determining, on a stress-strain curve beyond a region of the post-yield stress-strain slope, a region of substantially perfectly plastic behavior at a stress level $\sigma_{min}$; and determining a fracture load of the proximal femur, by a processor and based on (a) the elastic modulus, (b) the cortical bone yield strength, (c) the stress level $\sigma_{min}$, and (d) the post-yield stress-strain slope.

Some embodiments provide a method of modeling structural behavior of a femur under a loading condition representing forces due to a fall onto the greater trochanter of the femur, by a processor, beyond bone fracture. The method comprises determining, by a processor, a pre-fracture displacement of a femur and corresponding pre-fracture load supported by the femur for a given pre-fracture displacement; determining a maximum load supported by the femur prior to femur fracture; and determining a post-fracture displacement and corresponding post-fracture load supported by the femur for a given post-fracture displacement; wherein the post-fracture load decreases with increasing post-fracture displacement.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

The accompanying drawings, which are included to provide further understanding of the subject technology and are incorporated into and constitute a part of this specification, illustrate aspects of the disclosure and together with the description serve to explain the principles of the subject technology.

DETAILED DESCRIPTION

In the following detailed description, numerous specific details are set forth to provide a full understanding of the subject technology. It should be understood that the subject technology may be practiced without some of these specific details. For example, various methods disclosed herein are discussed with respect to the femur and hip. However, methods disclosed herein can be used to calculate the strength or fracture load of any of a variety of bones, including long bones, such as the femur, tibia, humerus, or radius, to name a few. Other bones can also be analyzed, including flat bones or vertebrae. In other instances, well-known structures and techniques have not been shown in detail so as not to obscure the subject technology.

Bone strength or fracture load modeling techniques have been unable to evaluate bone fracture load in a manner that provides a force versus displacement curve with a peak load. Most models produce force versus displacement curves that are linear in the elastic region and then have decreasing slope as various elements are predicted to yield and fail. However, the slope never becomes negative.

Figure 1B:
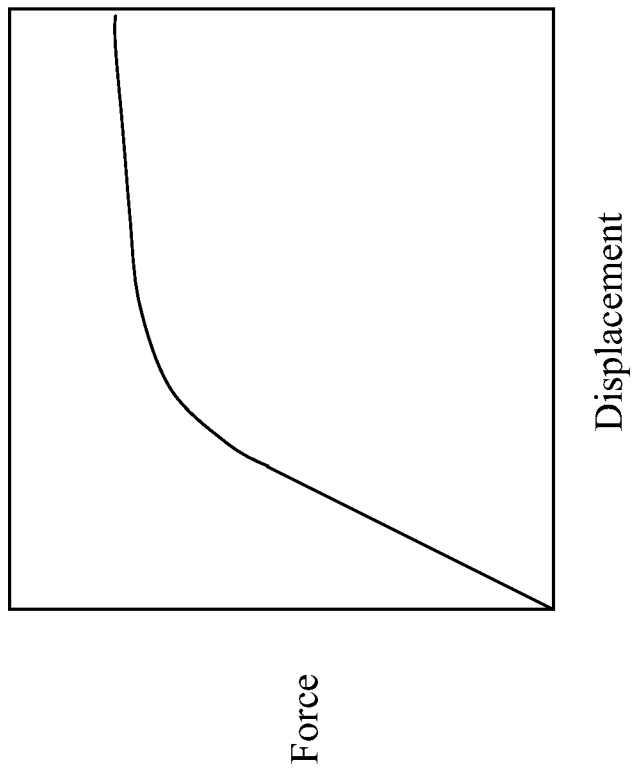
FIG. 1B is another force versus displacement curve, according to some techniques.
Figure 1A:
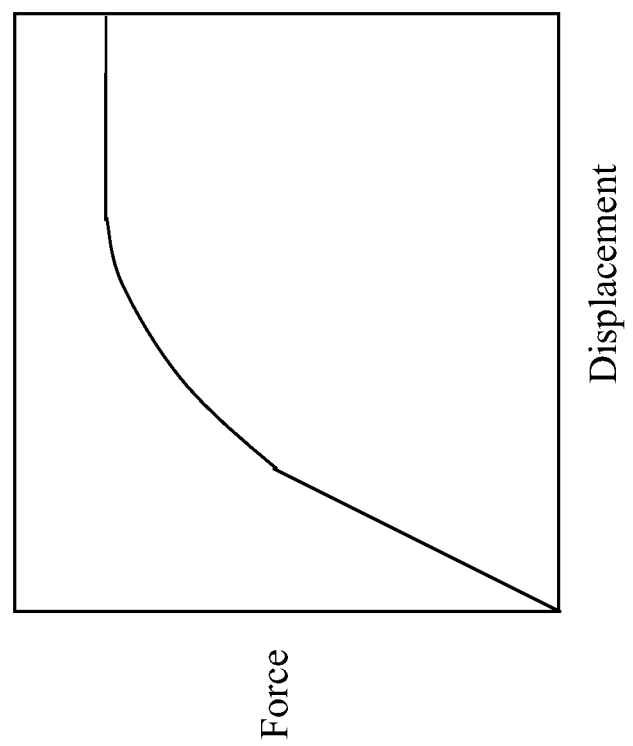
FIG. 1A is a force versus displacement curve, according to some techniques.

For example, FIGS. 1A and 1B illustrate examples of force versus displacement curves that fail to provide a peak load. These figures indicate that the bone has not actually fractured because it can still support the same force regardless of the amount of displacement or deformation as shown in FIG. 1A. Further, FIG. 1B illustrates that the bone can support a gradually increasing force as deformation increases regardless of the amount of deformation. These depictions of bone behavior from current models are inaccurate and unhelpful.

"Perfectly Plastic Material Behavior" Does not Create a Peak in a Force-Displacement Curve For example, a method reported in a paper by Oden et al. described a fall loading study. See Oden Z M, Selvitelli D M, Bouxsein M L, Effect Of Local Density Changes On The Failure Load Of The Proximal Femur, J. Orthop. Res. 17(5): 661-7, 1999 ("Oden"), which is incorporated herein by reference in its entirety. Oden indicates that the analysis was conducted by calculating the stresses and strains at each increment. These were then evaluated to determine the occurrence of yielding by using the maximum principal strain failure criterion.

In Oden's analysis, the maximum principal strain limits were 1.1% in compression and 0.78% in tension. Oden indicates that, "[i]f the strain at a particular integration point was greater than the maximum principal strain, the material properties at that integration point within the element were reduced, simulating an elastic, perfectly plastic material behavior." Oden also indicates that, "[t]he stresses were then recalculated, and there was an inspection for additional damage. This procedure continued until no more yielding occurred; then, the next increment began." As yielding began to occur, this signified the commencement of elemental failure. As more locations failed in subsequent increments, "the structural stiffness decreased and exhibited the typical knee on a stress-strain curve."

Although the Oden analysis used nonlinear FE modeling to evaluate the failure load of the proximal femur, Oden does not describe how the methodology could model the material behavior after failure. In particular, Oden states that the FE models simulated "an elastic, perfectly plastic material behavior." Accordingly, it does not follow how Oden could disclose or teach how to calculate a load-displacement curve with a load that increased, peaked, and then decreased as displacement increased. Oden simply does not provide an explanation or otherwise enable a person of skill in the art to create a load-displacement curve with a load that increased, peaked, and then decreased as displacement increased. Indeed, such a load-displacement curve with a peak could not be produced by the "elastic, perfectly plastic material behavior" used in Oden's analysis. Further, if an elastic, perfectly plastic material behavior were modeled in a simple, one-dimensional situation, the stress values at the locations of failure would remain constant as strain and displacement increased. Because stress would never decrease, the load supported by the model would also never decrease. Therefore, Oden's methodology would not have produced a force versus displacement curve with a peak.

Lack of a peak in the force versus displacement curve indicates that current models do not actually predict bone fracture. Thus, these models do not predict the case when the bone actually breaks (which causes an actual decrease in the load it can support), which is the most common clinical situation (e.g., a hip fracture). Models that do not predict a peak in the force versus displacement curve are not as useful as those showing a peak.

Estimating Deflection to Predict Ultimate Femoral Strength

Other techniques have employed an arbitrary method of defining whole bone strength or fracture load as the force at which there was 4% deformation of the femoral head relative to the greater trochanter. See Orwoll E.S. et al., Finite Element Analysis of the Proximal Femur and Hip Fracture Risk in Older Men, J. Bone Miner. Res. 2009, 24:475-83, which is incorporated herein by reference in its entirety. Without being bound by theory, this technique was used because there was no peak in the force-displacement curve. However, such methods could have used a 3% deformation, a 5% deformation, or a 6% deformation, etc. Four percent probably predicted the proximal femoral strengths most accurately (n=51, $r^2$=0.80, according to their cited unpublished data, where "n" is the number of proximal femora in the sample, and "r" is the sample correlation coefficient). This illustrates one of the advantages of the methods disclosed herein over previous methods. Previous methods did not result in a peak in the force-displacement curve, inconsistent with actual bone behavior. As a result, researchers needed to use alternative methods for specifying an estimated proximal femoral fracture load.

In accordance with at least one aspect of some embodiments disclosed herein is the realization there is a strong correlation between measured and FE computed fracture load for a posterolateral fall loading ($r^2$=0.81). Further, in some embodiments, lateral fall loading may be a better predictor of fracture than posterolateral fall loading, which indicates that lateral fall failure loads may be easier to predict than posterolateral failure loads. Thus, some methods disclosed herein can be used to predict the fracture load of a femur under a lateral fall load, with a $r^2$ that would be higher (just as it is for stance loading, which is also "in-plane," i.e., in the coronal plane).

Accordingly, as provided in some embodiments, the presence of a peak using methods disclosed herein provides the proper and accurate shape of the force-displacement curve. By including a peak load, the methods disclosed herein are able to more accurately represent the fracture process than previous methods. Some methods disclosed herein are also superior in that they can employ a definition of whole bone fracture load for the proximal femur that is objective and is not based on arbitrary criteria.

These and other factors enable embodiments of the methods disclosed herein to provide improved reliability when evaluating bone fracture load and the consequences of bone fracture. For example, methods disclosed herein can reliably evaluate proximal femur fracture load and the consequence of low proximal femur strength, such as hip fracture.

Therefore, methods disclosed herein can be used to assess the bone strength or risk of fracture, either clinically or in research. The bones evaluated can be any bone of the body, such as the femur, tibia, radius, vertebrae, etc.

In research, the technology can be implemented to evaluate the effect of new drug treatments to determine if they will reduce the risk of bone or hip fracture.

Moreover, methods disclosed herein may be useful to determine if cancer therapies may increase the risk of bone or hip fracture. This could lead to monitoring cancer patients who are being treated to determine if they need preventive medication. Currently, patients are started on osteoporosis medications after about one year, if needed. Employing methods disclosed herein would allow assessment of effects on bone or hip strength much sooner, making it valuable for preventative health care.

Further, methods disclosed herein can also be used to determine drug efficacy in increasing bone strength or fracture load. For example, methods can be used to aid pharmaceutical companies in evaluating drugs for clinical trials to determine hip strength in order to reduce fracture risk.

Embodiments Relating to Hip Strength and Fracture Risk Analysis

In accordance with some embodiments, methods are provided for estimating the strength of the hip (the proximal femur) for assessing osteoporosis and the risk of hip fracture. The methods can also be used for other applications for which the strength of the hip is important. As noted above, embodiments herein can be used for any of the bones. Thus, the present example relating to hip strength and fracture can be applied generally to other bones.

The strength of the proximal femur can be defined as the maximum force that can be applied to the femoral head before the bone will break and no longer be able to support the applied force.

In some models, this applied force or displacement (which inherently induces a force) is applied to the femoral head and constraints (which prevent the bone from moving at the constrained points) can be applied to the greater trochanter and the distal end of the model (often a transverse plane through the femoral shaft). Because certain forces are associated with the constrained aspects of the model, the strength of the proximal femur relates directly to the force on the greater trochanter. Indeed, because these forces on the femur are mathematically related to each other, other loading conditions or boundary conditions are generally equivalent. Mathematically, the sum of the forces applied to the model must equal zero because the bone does not move as a result of the forces (no net force, no movement).

For example, the model could be interpreted as constraining the femoral head in place, while a force or displacement is applied at the greater trochanter. Hence, a force at the greater trochanter could be called the strength (or applied force) of the femur. This force at the greater trochanter can be characterized as the force applied by the ground to the hip when a person falls on the hip.

Thus, it is possible to calculate the proximal femoral strength by instead applying a force to the greater trochanter and constraining the femoral head (in addition to constraining the distal end of the model). The model could then calculate the force at the femoral head, at the constraints. The femoral strength could be defined as either the maximum force on the femoral head or as the maximum force on the greater trochanter.

Proximal femoral strength can be estimated by combining imaging data of the bone, such as from quantitative computed tomography ("QCT") scan imaging, which provides the bone geometry and density at each point in the bone, with FE analysis. The imaging data can be obtained using x-ray computed tomography, computed axial tomography ("CAT" scan), magnetic resonance imaging ("MRI"), nuclear magnetic resonance imaging ("NMRI"), or magnetic resonance tomography ("MRT"), or other imaging techniques, as improvements and new imaging techniques develop, which can provide the bone geometry and density at each point in the bone, for an FE analysis. In accordance with some embodiments, the FE analysis can be used to calculate stresses, strains and/or other forces and deformations at a plurality of different regions or positions in the bone. In some implementations, the FE analysis can be used to make calculations for several, several hundred, tens of thousands, or hundreds of thousands of particular regions or positions. This analysis can be done, in some embodiments, using a computer.

For example, a FE analysis numerical technique subdivides a structure into many smaller parts (finite elements) which, together, explicitly represent the complex material heterogeneity and 3D bone geometry as a mathematical model. Force or displacement is then mathematically applied to represent a specific loading condition, such as single-limb stance or a particular type of fall onto the greater trochanter.

When a FE model is analyzed, stress and strain throughout the bone structure can be computed. This information is used in conjunction with material failure criteria in various ways to estimate the strength of the proximal femur under the particular loading condition. Collectively, this technique is called, "subject-specific CT scan-based finite element modeling for calculation of proximal femoral strength."

Various methodologies can be used to compute an elastic modulus of each element. The elastic modulus (E), or modulus of elasticity, relates to stress and strain under uniaxial loading using the following formula:

$$E = \frac{\text{Stress}(\sigma)}{\text{Strain}(\varepsilon)}$$

The stress-strain state can also be determined using more complex equations. For example, an element in the femur can be exposed to stress and strain in 3 directions at once (a triaxial stress state). In accordance with some embodiments, the elastic modulus of each element can be calculated by first computing the elastic modulus of each voxel within the element from a calibrated CT scan density of the voxel using modulus-density relationships. The elastic moduli can then be averaged while accounting for the volume fractions of the voxels to create an "element modulus." This element modulus produces a result different from an averaging of the densities of the voxels due to the nonlinear relationship between elastic modulus and density.

For linear models, the strength of each element (with yield and ultimate strength assumed equal) can be calculated using the same methodology as for the elastic modulus, but using strength-density relationships rather than modulus-density relationships. However, for nonlinear modeling, the strength can be determined using a slightly different procedure. First, the "effective" density is back-calculated from the modulus-density relationship. This single density value for the element is then used to calculate the strength of the element using a strength-density relationship. Thus, unlike the elastic modulus, the material strength of the element is not directly calculated from the voxel density data.

The FE modeling method was further improved for single-limb stance loading by using nonlinear material properties and nonlinear modeling that can represent the process of applying a displacement or force to the femoral head which can cause gradually increasing localized fracture within the bone, followed by subsequent failure of the whole bone, commonly called a fracture or broken bone. See Keyak J H, Improved Prediction Of Proximal Femoral Fracture Load Using Nonlinear Finite Element Models, Med. Eng. Phys. 23:165-173, 2001. [Corrigendum published 25:615, 2003], which is incorporated herein by reference in its entirety. This method was refined to be more accurate and to show validity for bones with tumors. See Keyak J H, Kaneko T S, Tehranzadeh J, Skinner H B, Predicting Proximal Femoral Strength Using Structural Engineering Models, Clin. Orthop. Rel. Res. 2005;437:219-28, which is incorporated herein by reference in its entirety. The nonlinear methodology for stance loading and the linear methodology for fall loading have also been described. See Keyak J H, Koyama A K, LeBlanc A, Lu Y, Lang T F, Reduction In Proximal Femoral Strength Due To Long-Duration Spaceflight, Bone 2009;44:449-53, which is incorporated herein by reference in its entirety.

The above methods of evaluating the strength of the proximal femur for a fall onto the greater trochanter rely on linear material properties and linear modeling. However, this approach can provide only limited accuracy because it can only model up to the onset of bone fracture, and not beyond bone fracture.

Thus, some embodiments disclosed herein provide unique nonlinear modeling of material properties, allowing for modeling the bone behavior through the fracture process. For example, as increasing displacement is applied to the femoral head, the bone first deforms elastically. Then, as displacement and, therefore, force are increased, the bone experiences damage due to overloading, often first in the trabecular or cancellous bone (which is called a bone bruise). Then displacement increases up to and beyond the point at which the maximum load is reached (the strength, also known as the fracture load). After the maximum load is achieved and displacement of the femoral head continues, the load that the bone can support decreases and the bone fractures. During the FE analysis of methods disclosed herein, the analysis computes the force required to achieve the applied displacement and the bone fracture load, i.e., a force versus displacement curve, which is analogous to the force versus displacement curve that is measured during mechanical testing. The computed proximal femur strength is the peak force in this curve.

Figure 2:
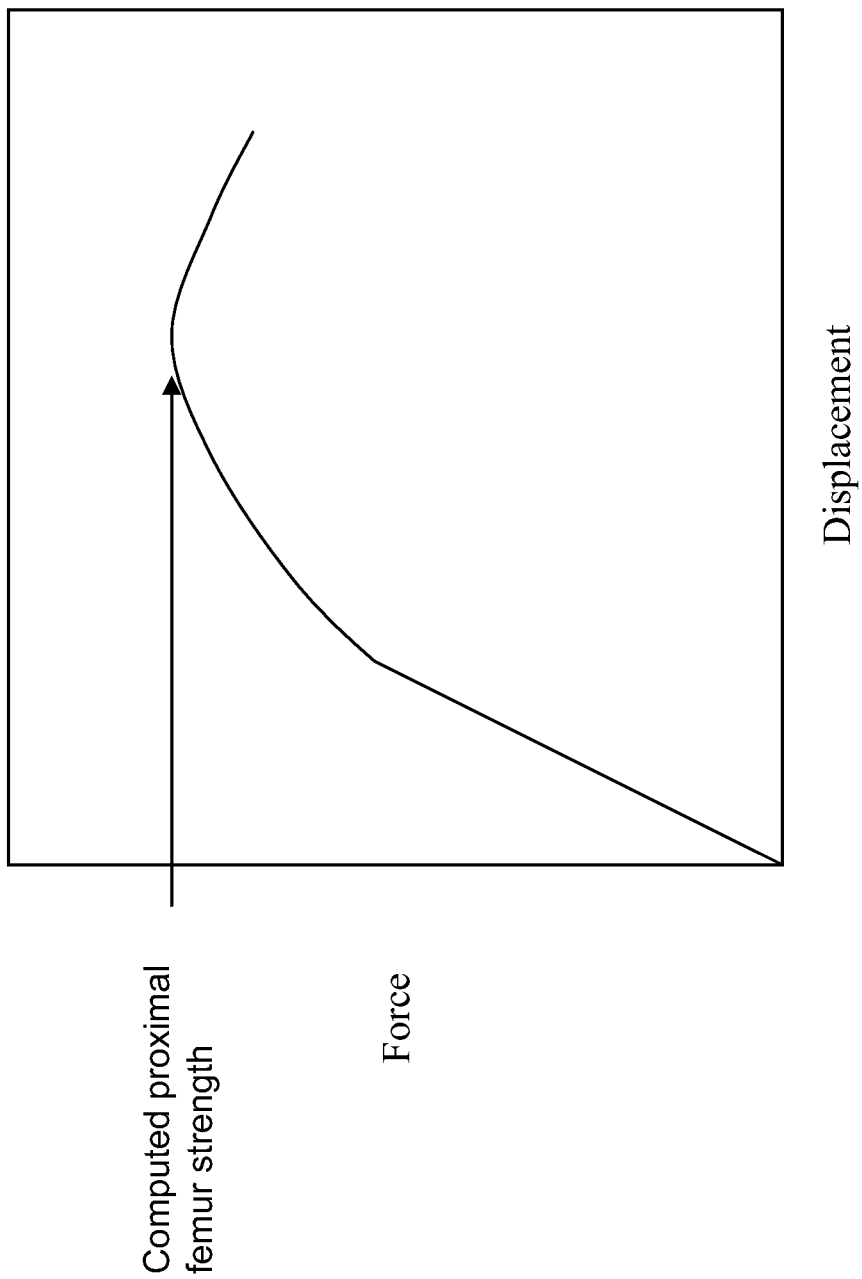
FIG. 2 is a force versus displacement curve illustrating a peak representative of predicted proximal femur strength or fracture load, according to some embodiments.

Some methods disclosed herein for modeling fall loading can provide a force versus displacement curve that is initially linear (when no damage to the bone has occurred), and that then exhibits decreasing slope as the bone begins to be damaged. Then a peak is reached (the predicted proximal femur strength) and the slope becomes negative, as shown in FIG. 2.

Some methods disclosed herein for computing proximal femoral strength for impact from a fall onto the greater trochanter can be patterned after nonlinear modeling for single-limb stance loading. Some methods disclosed herein employ heterogeneous nonlinear material properties that are based on the density at each point in the bone, as evaluated from a QCT scan of the bone.

However, the material properties used for the fall loading models can be different from those for stance loading. Without being bound by theory, this may be because bone behaves differently when it is loaded in different directions (i.e. bone is anisotropic). The current models employ isotropic material properties, so the properties should be modified if the loading conditions are considerably different (e.g., stance loading which is applied essentially vertically versus loading from a fall onto the greater trochanter, which is applied transversely).

In some embodiments, orthotropic properties can be used to model bone. However, such a level of complexity may not be necessary to achieve an accurate model. Further, bone is weaker in tension than in compression, and this effect can be optionally modeled, but it is not necessary. In some embodiments, although counterintuitive, the omission of these two modeling aspects advantageously makes the models simpler, and the models actually predict proximal femur strength quite precisely. However, some methods disclosed herein can also be modified to include different properties in tension and compression which may further improve accuracy.

According to some embodiments, methods disclosed herein comprise computing a force versus displacement curve that reaches a peak and predicts values of the proximal femur fracture load with acceptable precision. For elements representing cortical or compact bone, the cortical bone strength can be set to one-half the strength of the strongest trabecular bone in the model.

Where the cortical bone strength is set to one-half the strength of the strongest trabecular bone in the model, the value of one-half can assume that the elastic moduli are as specified previously for the stance and fall models. If the elastic moduli were changed, the strength values can be changed by an amount to compensate for the reduction in elastic moduli. Generally, the strength of the cortical bone can be reduced by an amount relative to that of the trabecular bone in order to obtain a force versus displacement curve with a peak force.

Although the cortical bone strength does not need to be constant, a constant value appears to be adequate and variable strengths depending on density do not improve the accuracy of the models disclosed herein.

In some embodiments, the elastic modulus does not need to be modified to analyze different loading conditions. This result is surprising, but consistent with the use of isotropic properties. This approach was used because the linear FE models predicted the proximal femoral strength fairly precisely and because using the same moduli for all models is a useful feature for comparing models with different loading conditions. Generally, if the elastic moduli of all elements were changed by a constant factor, the stress values would not change (because the cross-sectional area of the bone would not change). Thus, the result would be essentially the same.

Figure 3:
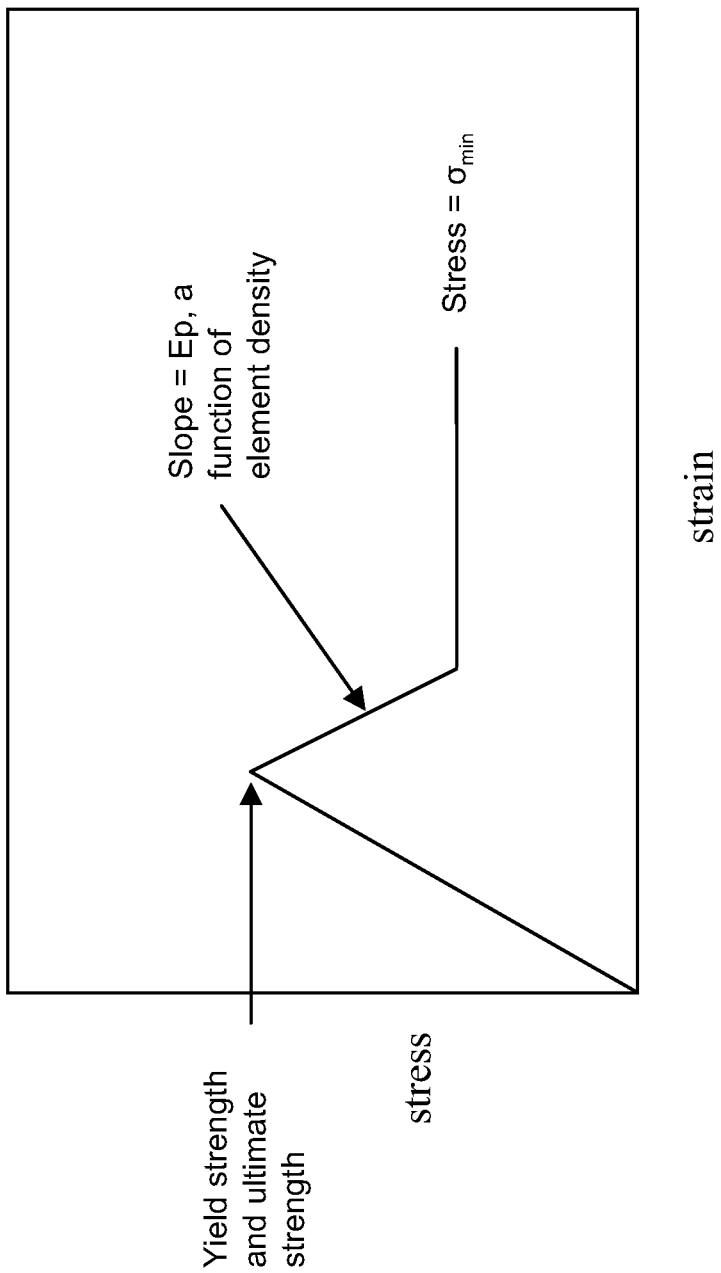
FIG. 3 is a representation of a stress-strain curve of an element, according to some embodiments. The elastic modulus is the slope of the first (leftmost) linear portion of the stress-strain curve.

In some embodiments, additional material properties can also be defined. For example, a stress-strain curve can be specified for each element based on its effective density, as determined from the elastic modulus of the element as shown in FIG. 3. Similarly, additional properties could be specified, such as yield strength and ultimate strength of the bone. The yield strength and ultimate strength of the bone can be different. However, the yield strength and ultimate strength of the bone may be assumed to be the same, and no plastic strain before the downward portion of the stress-strain curve was modeled.

The slope after yield, Ep, can be a function of the element density. When the stress reaches the value $\sigma_{min}$, the element exhibits perfectly plastic behavior. Generally, the stress level $\sigma_{min}$ can be determined as the product of X and S. In some embodiments, X can be between from about 0.22 to about 0.62. In some embodiments, X can be between from about 0.32 to about 0.52. Further, X can be between from about 0.37 to about 0.47. For example, X can be about 0.42. Additionally, S can be the strength of the bone. A similar approach had been used for the single-limb stance models except, for fall loading, perfectly plastic deformation was assumed to occur immediately after yield strength was reached.

In some embodiments, the cortical bone yield strength can be calculated as from about one-third to about two-thirds of the strength of the strongest trabecular bone. The cortical bone yield strength can be calculated as from about 40% to about 60% of the yield strength of the strongest trabecular bone. The cortical bone yield strength can be calculated as about 50% or half of the strength of the strongest trabecular bone. The trabecular bone yield strength can be varied to achieve the optimal prediction of proximal femoral strength.

Excellent results were obtained when the following relationship was used for trabecular bone yield strength:

$$S_{Trabecular\_Bone\_Strength} = 102.0(denash)^X,$$

where denash is the apparent ash density in g/cm$^3$, X is the exponent, and $S_{Trabecular\_Bone\_Strength}$ is the yield and ultimate strength (assumed to be the same) in MPa. The exponent X can be from about 1.4 to about 1.6. In some implementations, the exponent X is about 1.5.

For comparison, note that the relationship that was used for stance loading was different:

$$S_{Stance\_Loading} = 102.0(denash)^{1.7989},$$

which was obtained from experimental measurements on pieces of bone.

A density cutoff above which the bone is assumed to be cortical bone was also optimized and was found to be an apparent ash density of 0.6037 g/cm3. This was also the density at which the cortical and trabecular bone relationships for Ep versus apparent ash density intersect. The modulus and strength relationships (one of each) were used for both cortical bone and trabecular bone, so this density cutoff was for specifying material behavior at or beyond the ultimate strength. Thus, in some embodiments, the apparent ash density can be about 0.6037 g/cm3. However, the apparent ash density can be from about 0.5890 g/cm3 to about 0.6100 g/cm3.

Although in some embodiments, the apparent ash density can be used, other measures of bone density can also be used. For example, in addition to apparent ash density, the dry density or wet density of bone can be used. These different measures of bone density are related to each other. Further, the tissue density can be used in combination with the "bone volume fraction" (bone tissue volume divided by total volume). In some implementations, apparent density can be calculated as the tissue density multiplied by the bone volume fraction.

The equations for Ep and $\sigma_{min}$ were also optimized. The prediction of proximal femoral strength was optimal when Ep was about 60 times that for stance loading. Thus, for trabecular bone, $$Ep_{Trabecular\_Bone} = 60(Ep_{Stance}) = 60(-2083.6(denash)^{1.447}) Mpa,$$

and for cortical bone, $$Ep_{Cortical\_Bone} = 60(Ep_{Stance}) = 60(-1003.8) = -60,228 \text{ Mpa}.$$

For $\sigma_{min}$, note that, for stance loading, $$\sigma_{min\_Stance\_Loading} = 43.087(denash)^{1.8093}.$$

Thus, for stance loading, $$\frac{\sigma_{min\_Stance\_Loading}}{S_{Stance\_Loading}} = \left(\frac{43.087}{102}\right)(denash)^{(1.8093-1.7989)}.$$

The exponent is very small, so $$\frac{\sigma_{min\_Stance\_Loading}}{S_{Stance\_Loading}} = 0.422, \text{ or}$$

$$\sigma_{min\_Stance\_Loading} = 0.422(S_{Stance\_Loading}),$$

for stance loading.

This same relationship was tested for fall loading and the coefficient of $S_{Stance\_Loading}$ (0.422) was varied. This equation, $$\sigma_{min\_Fall\_Loading} = 0.422(S_{Fall\_Loading}),$$

was found to be excellent for predicting femoral strength under fall loading as well.

The apparent ash density can be obtained from QCT data by first calibrating the data using a calcium hydroxyapatite ("CHA") calibration phantom (Image Analysis, Inc., Columbia, Ky.) to obtain the CHA equivalent density. In some embodiments, other calibration phantoms, such as those that use $K_2HPO_4$ instead of CHA, are also available to calculate apparent ash density and other densities. Using CHA equivalent density, the apparent ash density can then be obtained using the equation:

$$denash = 0.00088703(den) + 0.063343,$$

where den is the CHA equivalent density in $mg/cm^3$ and denash is in $g/cm^3$. See Keyak J H, Kaneko T S, Tehranzadeh J, Skinner H B, Predicting Proximal Femoral Strength Using Structural Engineering Models, Clin. Orthop. Relat. Res., August (437):219-228, 2005, which is incorporated herein by reference in its entirety. The elastic modulus can then be calculated using:

$$E = 14942(denash)^{1.8601}.$$

To create the nonlinear models, since the elastic modulus had already been computed by averaging values over all voxels in each element, an effective ash density for each element was used to compute the post-failure properties from the inverse relation:

$$denash = \left(\frac{E}{14942}\right)^{\left(\frac{1}{1.8601}\right)}.$$

Below is FORTRAN code that can be used to implement some embodiments of the methods disclosed herein ("c" indicates a comment line):

```
if(denash.le.0.6037)then
c      trabecular bone
c      This is for stance loading for all bone
c      S=102.0*(denash**1.7989)
c      This is for nonlinear fall
S=102.0*(denash**1.50)
else
c      For fall loading, need to reduce the strength of cortical bone
c      to get a decrease in force with increasing displacement.
c      S(0.6037)/2=102.0*(denash**1.50)/2 when denash=0.6037
c      or S=102.0*(0.6037**1.50)/2 =23.9
S=23.9
endif
c      Specify 3rd line -- point that defines rate of downward slope
c      and start of perfect plasticity after that
c      That's nominal plastic strain = eABpr + (sigma_min-S)/Eppr
c      Call that eACprime
```

```
if(denash.le.0.6037)then
c      trabecular bone
Ep= -2083.6*(denash**1.447)
c      Above is for stance loading. For nonlinear fall increase Ep
Ep=Ep*60
else
c      cortical bone.
Ep= -1003.8
c      Above is for stance loading. For nonlinear fall increase Ep
Ep=Ep*60
endif
```

Ep can be adjusted to account for the size of the element (because it is not a true "material property," independent of size). This is described in Table 1 in Keyak J H, Kaneko T S, Tehranzadeh J, Skinner H B, Predicting Proximal Femoral Strength Using Structural Engineering Models, Clin. Orthop. Relat. Res., August (437):219-228, 2005, which is incorporated herein by reference in its entirety. For simplicity, the adjustment for trabecular bone can be used for cortical bone as well. The corrected value of Ep is called Eppr:

```
c              Eppr = (3.*E*Ep) / (E*15. - (15.-3.)*Ep)
Eppr = (3.*E*Ep) / (E*15. - 12.*Ep)
c              sigma_min = 43.087 * (denash** 1.8093)
c              note that Sigma_min/S=43.087/102
               (denash)**(1.8093-1.7989) = 0.422 *
               denash**0.0104
c              denash**0.0104 is very close to 1.
sigma_min=0.42*S
```

For clarity, without the comment lines, the FORTRAN code that can implement an embodiment of the methods disclosed herein is as follows:

```
if(denash.le.0.6037)then
S=102.0*(denash**1.50)
else
S=23.9
endif
if(denash.le.0.6037)then
Ep= -2083.6*(denash**1.447)
Ep=Ep*60
else
Ep= -1003.8
Ep=Ep*60
endif
Eppr = (3.*E*Ep) / (E*15. - 12.*Ep)
sigmamin=0.42*S
```

As illustrated in the above-described methodology, some embodiments can employ the von Mises stress or distortion energy theory of failure to identify yielding of the bone. However, it is understood that analogous procedures can be implemented for use with alternate failure theories, such as strain-based failure theories, using established relationships in the field of structural analysis.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable by different embodiments of the disclosure in order to be encompassed within the scope of the disclosure.

What is claimed is:

1. A computer implemented method for modeling structural behavior of a bone under a load, the method comprising:
   determining, using a numerical modeling method, an elastic modulus (E) based on a bone density at each of a plurality of regions of the bone, determined by an imaging technique;
   determining, using a processor, a cortical bone yield strength as a fraction of a trabecular bone yield strength;
   determining, using the processor and based on the plurality of densities, a post-yield stress-strain slope of the bone, wherein the slope is less than zero;
   determining, using the processor, on a stress-strain curve beyond a region of the post-yield stress-strain slope, a region of perfectly plastic behavior at a stress level $\sigma_{min}$; and
   determining, using the processor, a fracture load of the bone in response to an applied displacement, and based on (a) the elastic modulus, (b) the cortical bone yield strength, (c) the stress level $\sigma_{min}$, and (d) the post-yield stress-strain slope.

2. The method of claim 1, wherein the fracture load comprises a peak strength.

3. The method of claim 1, wherein $\sigma_{min}$ is the product of X and S, wherein X is between 0.22 and 0.62 and S is a yield strength of trabecular bone.

4. The method of claim 1, wherein the fraction ranges from about ⅓ to about ⅔.

5. The method of claim 4, wherein the fraction is about ½.

6. The method of claim 1, wherein the bone fracture load is determined while maintaining an elastic modulus of the bone constant for all loading conditions.

7. The method of claim 1, wherein the bone comprises a femur.

8. The method of claim 1, wherein the numerical modeling method used is a finite element analysis method.

9. A method for evaluating the efficacy of a drug in increasing bone fracture load to reduce fracture risk in a patient, the method comprising:
   calculating a first bone fracture load;
   after a drug therapy, calculating a second bone fracture load; and
   comparing, using a processor, the first bone fracture load and the second bone fracture load to determine an effect of the drug therapy on bone fracture load;
   wherein the first and second bone fracture loads are determined by:
   calculating, using a numerical modeling method, an ash density of a bone based on imaging data;
   determining, using the processor, cortical bone yield strength as a fraction of trabecular bone yield strength, based on the ash density; and
   determining, using the processor, a fracture load of the bone based on the cortical bone yield strength.

10. The method of claim 9, wherein the bone comprises a femur.

11. The method of claim 9, wherein the cortical bone yield strength is from about ⅓ to about ⅔ of the trabecular bone yield strength.

12. The method of claim 11, wherein the cortical bone yield strength is about ½ of the trabecular bone yield strength.

13. The method of claim 9, wherein the trabecular bone yield strength is calculated as $102*(\text{ash density})^{1.5}$.

14. The method of claim 13, wherein the ash density is calculated as $0.00088703*(\text{den})+0.063343$, where den is a calcium hydroxyapatite ("CHAD") equivalent density.

15. The method of claim 9, wherein the first and second bone fracture loads are determined while maintaining an elastic modulus of the bone as constant for all loading conditions.

16. The method of claim 9, wherein the numerical modeling method used is a finite element analysis method.

17. A method of modeling structural behavior of a bone, under a loading, condition, beyond bone fracture, the method comprising:
   determining, by a processor, a pre-fracture displacement of a bone and corresponding pre-fracture load supported by the bone for a given pre-fracture displacement, the corresponding pre-fracture load being based on (a) an elastic modulus, (b) a cortical bone yield strength, (c) a stress level $\sigma_{min}$ at perfectly plastic behavior and (d) a post-yield stress-strain slope, for one or multiple parts of the bone;
   determining, using the processor, a maximum load supported by the bone prior to bone fracture; and
   determining, using the processor, a post-fracture displacement and corresponding post-fracture load supported by the bone for a given post-fracture displacement;
   wherein the post-fracture load decreases with increasing post-fracture displacement.

18. The method of claim 17, wherein the cortical bone yield strength is from about ⅓ to about ⅔ of trabecular bone yield strength.

19. The method of claim 18, wherein the cortical bone yield strength is about ½ of the trabecular bone yield strength.

20. The method of claim 18, wherein the trabecular bone yield strength is calculated as $102*(\text{ash density})^{1.5}$.

21. The method of claim 20, wherein the ash density is calculated as $0.00088703*(\text{den}) +0.063343$, where den is a calcium hydroxyapatite ("CHA") equivalent density.

22. The method of claim 17, wherein determining a maximum load supported by the bone prior to bone fracture and determining a post-fracture displacement and corresponding post-fracture load supported by the bone are done using a numerical modeling method; and
   wherein the numerical modeling method used is a finite element analysis method.

* * * * *